United States Patent
Arnold

Patent Number: 5,989,273
Date of Patent: Nov. 23, 1999

[54] APPARATUS FOR PRODUCING HAIR TRANSPLANTATION DONOR STRIPS AND METHODS

[76] Inventor: James E. Arnold, 24142 Big Basin Way, Saratoga, Calif. 95070

[21] Appl. No.: 08/810,930

[22] Filed: Mar. 5, 1997

Related U.S. Application Data

[63] Continuation-in-part of application No. 08/757,417, Nov. 27, 1996, abandoned, which is a continuation of application No. 08/375,313, Jan. 18, 1995, abandoned.

[51] Int. Cl.⁶ ................................................. A61B 17/32
[52] U.S. Cl. ........................ 606/167; 606/133; 606/131
[58] Field of Search .............................. 606/1, 131, 133, 606/167, 170, 171, 174, 184, 185

[56] References Cited

U.S. PATENT DOCUMENTS

| | | |
|---|---|---|
| 4,911,159 | 3/1990 | Johnson et al. . |
| 5,026,385 | 6/1991 | Schutte et al. . |
| 5,269,801 | 12/1993 | Shiau . |
| 5,439,475 | 8/1995 | Bennett . |
| 5,447,516 | 9/1995 | Gardner .................................. 606/167 |
| 5,454,384 | 10/1995 | McAllister .............................. 606/167 |
| 5,713,375 | 2/1998 | McAllister .............................. 606/167 |
| 5,858,019 | 1/1999 | Ashraf ..................................... 606/167 |

FOREIGN PATENT DOCUMENTS

WO 96/06566  3/1996  WIPO .

OTHER PUBLICATIONS

*Multiple Blade Holder*, Byron Medical Brochure© 1993, Tucson, Arizona.

*Robbins Universal Scalpel Handle*, Robbins Instruments, Inc. Brochure, Chatham, New Jersey.

*Van Sickle Multiple Blade Holders*, Van Sickle Surgical Instrument Co. Brochure, Dallas, Texas.

*Primary Examiner*—Glenn K. Dawson
*Attorney, Agent, or Firm*—Townsend and Townsend and Crew LLP

[57] ABSTRACT

The invention provides methods and apparatus for producing hair transplantation donor strips for use in hair transplantation procedures. According to one exemplary method, a surgical instrument is provided having at least two planar blades, with each blade having a sharpened edge, and with the blades being substantially parallel to each other. The blades are translated along and through an area of the scalp having hair to form at least two parallel incisions in the scalp. The orientation of the blades relative to the hair is adjusted such that the blades are generally aligned at all times with the direction of hair growth for the hair between the blades when the surgeon is making the incisions. A graft of skin having hair is then removed from between the incisions formed by the blades. At least a portion of the graft of skin having at least one hair is then placed into another area of the scalp.

18 Claims, 8 Drawing Sheets

APPARATUS FOR PRODUCING HAIR TRANSPLANTATION DONOR STRIPS AND METHODS

CROSS REFERENCE TO RELATED APPLICATIONS

This application is a continuation in part application of U.S. patent application Ser. No. 08/757,417, filed Nov. 27, 1996, abandoned, which is a continuation of U.S. patent application Ser. No. 08/375,313, filed Jan. 18, 1995, now abandoned. The complete disclosure of all these applications are herein incorporated by reference.

BACKGROUND OF THE INVENTION

This invention relates to methods and apparatus for hair transplantation, and in particular to the production of hair transplantation donor strips, i.e. elongate strips of skin having hair, that are removed from the scalp for subsequent transplantation to another area of the scalp.

In a typical hair transplantation procedure, grafts of skin containing hair are removed from the scalp and are transplanted to another area of the scalp. To place the removed grafts into these areas, a number of incisions are first made in the scalp. The incisions are then cleaned and the grafts are inserted into the incisions. When placing the grafts into the incisions, the surgeon attempts to arrange the grafts so that the resulting transplant resembles a normal hairline. To accomplish such a task, it is usually desirable to place only a small number of hairs, e.g., two to six (referred to as a minigraft), or even a single hair (referred to as a micrograft) into the incisions. Exemplary methods and apparatus for hair transplantation are described in co-pending U.S. patent application Ser. No. 08/375,312, filed Jan. 18, 1995 (Attorney Docket No. 16798-1-1), now U.S. Pat. No. 5,611,810, the disclosure of which is herein incorporated by reference. An exemplary apparatus for forming incisions to receive minigrafts is described in co-pending U.S. patent application Ser. No. 08/375,314, filed Jan. 18, 1995 (Attorney Docket No. 16798-2-1), now U.S. Pat. No. 5,693,064, the disclosure of which is herein incorporated by reference.

When performing a hair transplantation procedure, it is common to transplant a large number of grafts, usually about 500 to 600, in one operation. To obtain such a large number of grafts, it is desirable to remove the grafts from the scalp in elongate strips (referred to as donor strips). The donor strips are then separated into smaller grafts having about 1 to 6 hairs and used as transplants.

A prior art apparatus for producing donor strips is shown in FIG. 1. The apparatus includes a multiple blade holder 10. The holder 10 includes a knurled cylindrical handle 12 having a distal end 14 for holding a plurality of blades 24 (see FIG. 2). The blades 24 have a planar geometry and have a sharpened edge. The blades 24 are provided with holes which are received over a pair of pins 16, 18 at the distal end 14. The pin 18 is threaded for receiving a nut 20 which is used to secure the blades 24 to the holder 10. From the top view, the nut 20 is received on the right-hand side of the holder 10. Spacers 26 (see FIG. 2) are provided between the blades so that the blades are held spaced-apart from each other. In this way, a plurality of parallel blades can be held at the distal end 14. To load the blades 24 on the holder 10, the holder 10 is held in the left hand and the blades 24 and spacers 26 are placed over the pins 16, 18 with the right hand. The right hand is then used to apply and tighten the nut 20. The handle 12 includes a groove 22 for receiving the thumb of the surgeon when the handle 12 is grasped.

A prior art method for using the holder 10 of FIG. 1 to produce donor strips is illustrated in FIG. 2. The holder 10 includes three blades 24 that are spaced-apart by spacers 26. Initially, a portion of a patient's head 28 is shaved to produce a uniform hair length of about 3 mm from which the strips will be taken. The holder 10 is then grasped by a hand 30 with the thumb 32 resting in the groove 22. In this way, the hand 30 is held over the holder 10. The blades 24 are then pressed in to the patient's scalp, and the holder 10 is translated, usually in a single and continuous stroke, the length of the shaved area. This produces three parallel incisions along the patient's scalp. The skin lying within the incisions is then removed from the patient's scalp to produce two donor strips.

A serious drawback to the method illustrated in FIG. 2 is that the incisions are usually made without taking into consideration the direction of hair growth in the patient's scalp. Hair grows from the scalp in a variety of directions and varies both from patient to patient and from one area on the scalp to another. In the prior art method, the blades 24 are translated through the scalp in one continuous stroke, which severs some of the hair follicles from the hair. The grafts having these hairs cannot be used for transplantation. When making a single long sweep across the patient's scalp, a significant amount of the viable donor strip can be destroyed. In some cases it is possible to destroy up to about 80% of the viable strip. Grasping of the holder 10 in the manner shown in FIG. 2 contributes to the amount of destruction of the viable strip since such a grip requires translation of both the arm and hand and therefore makes it difficult to control the orientation of the blades when making the incisions.

It would therefore be desirable to provide methods and apparatus for producing hair transplantation donor strips with minimal or no loss of hairs in the strip when the strip is cut and removed from the scalp. Such methods and apparatus should be both efficient and easy to use. The methods and apparatus should further be able to compensate for the varied direction of hair growth in the patient's scalp when forming incisions to produce the donor strips.

SUMMARY OF THE INVENTION

The invention provides methods and apparatus for transplanting hair, and in particular to the production of hair transplantation donor strips with little or no destruction of hair follicles in the strips when the strips are cut and removed from the scalp. According to one exemplary method, a surgical instrument is provided having at least two planar blades that are substantially parallel, with each blade having a sharpened edge. In one step of the method, the blades are translated along and through an area of the scalp having hair to form at least two parallel incisions in the scalp. When making the incisions, the orientation of the blades relative to the hair is adjusted such that the blades are generally aligned, i.e. substantially parallel, at all times with the direction of hair growth for the hair between the blades. In this way, the incisions are made parallel to the hairs growing between the incisions so that the hair follicles are not severed from the hair when forming the incisions. A strip of skin having hair is then removed from between the incisions. At least a portion of the strip of skin having at least one hair is then placed into another area of the scalp.

Preferably, the entire length of skin between the incisions is removed in an elongate strip, referred to as a donor strip. If three or more blades are used to form the incisions, a plurality of donor strips are formed with a single cutting operation.

In an exemplary aspect, the instrument is grasped between the thumb and at least one finger and the finger is translated toward the wrist. While translating the finger towards the wrist, the wrist is maintained in a fixed position relative to the scalp. In this way, the blades are translated by movement of the finger, rather than by axial translation of the wrist or arm. Such a step provides improved control over the orientation of the blades to ensure that the blades remain parallel to the direction of hair growth at all times.

In another aspect, translation of the blades is ceased after the finger has been translated toward the wrist. The wrist is then repositioned axially away from the incisions and the step of translating the finger toward the wrist is repeated to increase the length of the incisions formed by the blades. In still a further aspect, the surgical instrument includes a groove near and generally parallel to the plane of the blades. A finger is held in the groove while translating the blades. The groove serves as a reference point for the surgeon when orienting the blades relative to the scalp. The groove also provides for a constant spatial relationship between the tips of the blades and the fingers. Such a relationship is advantageous when forming incisions since the tips of the blades are hidden beneath the scalp. By knowing the location of the blade tips relative to the surgeon's fingers, the depth of the resulting incision can more precisely be controlled. In a further aspect, the groove also provides for easier gripping of the instrument.

The invention provides an exemplary surgical apparatus for forming parallel incisions in the skin. The apparatus includes an elongate shaft having a proximal end and a distal end. A plurality of parallel spaced-apart planar blades are included at the distal end of the shaft. The shaft is tapered from the distal end to the proximal end such that the center of mass of the device is near the distal end of the shaft. Centering of the mass near the distal end is advantageous in improving the control of the blades when forming an incision.

In one aspect, a groove is included at the distal end of the shaft. The groove is provided for receiving a finger when the shaft is grasped by a surgeon. Preferably, the groove is aligned in a plane that is parallel with the plane of the blades. In another aspect, the shaft is constructed of stainless steel. In still a further aspect, the shaft has a smooth exterior surface.

The invention provides an improved surgical apparatus for forming parallel incisions in the skin. The apparatus is of the type that includes an elongate shaft having a proximal end and a distal end. A plurality of parallel spaced-apart blades are held at the distal end of the shaft, with the blades being held by a threaded pin and a nut. The apparatus is improved by tapering the shaft from the distal end to the proximal end such that the center of mass of the apparatus is near the distal end, and by forming a groove in the shaft opposite the side of the shaft having the nut. In this way, a right-handed surgeon can load the blades onto the apparatus from the left hand side of the apparatus. When loading the apparatus from the left hand side, the nut will be located on the left side of the apparatus so that it will not interfere with the right handed grip of the surgeon during an operation. In one particular aspect, the groove is formed in the shape of an hourglass. Alternatively, the groove has a half round geometry, i.e. semi-cylindrical.

The invention still further provides an exemplary surgical apparatus that is useful in performing parallel incisions in the skin. The apparatus comprises an elongate shaft having a proximal end and a distal end. At least two surfaces are provided at the distal end, with the surfaces preferably being intersecting. A plurality of parallel spaced-apart planar blades are provided at the distal end of the shaft. Each of the blades has a proximal end, a distal end, a top and a bottom. The blades are arranged such that one of the surfaces is adjacent the top of the blades to prevent the blades from rotating when translated through skin.

In one exemplary aspect, a securing mechanism is provided to hold the blades to at least one of the surfaces. Preferably, the blades are secured to the surface by providing a slot within each of the blades which may be in inserted over a single pin extending from one of the surfaces. A nut or other clamping device may then be employed to cinch the blades to the surface.

One particular advantage of such an arrangement is that a single pin may be employed to hold a plurality of blades in a parallel and spaced apart relationship. Rotation of the blades while performing a procedure is prevented by the other surface which is preferably orthogonal to the surface having the pin. Such a configuration is also advantageous in that it allows the blades to be staggered relative to each other. This may be conveniently be accomplished by sliding the blades along the pin until the distal ends of the blades are at a desired orientation. At this point, the securing mechanism is employed to cinch the blades to one of the surfaces, while the other surface prevents rotation of the blades during a procedure.

In another exemplary aspect, at least one spacer is provided between the blades to keep the blades both spaced apart and parallel to each other. In another aspect, the shaft is tapered from the distal end to the proximal end so that the center of mass of the apparatus is toward the distal end, near where the surgeon will grasp the shaft.

The invention further provides an exemplary method for forming parallel incisions in the skin. According to the method, a surgical device is provided which comprises an elongate shaft having a proximal end and a distal end. At the distal end are at least two surfaces. A plurality of blades are attached to the distal end, with the blades being spaced apart and parallel to each other. Further, the blades are arranged such that one of the surfaces is disposed over a top of the blades. The blades are then translated through the skin to form a plurality of parallel incisions in the skin. As the blades are translated through the skin, the surface disposed over the top of the blades prevents the blades from rotating.

In a preferable aspect, each of the blades includes a slot and the surgical device includes a securing mechanism comprising a pin extending from one of the surfaces. In this manner, the blades may be conveniently inserted over the slot and secured to one of the surfaces with the securing mechanism. Preferably, the pin will be threaded and a threaded nut will be employed to cinch the blades to the surface. Such an arrangement also allows the surgeon to adjust the orientation of the blades relative to each other so that the distal end of the blades are staggered relative to each other. This configuration is advantageous in that the surgeon is able to more easily translate the blades through uneven surfaces while keeping the blades generally parallel to the direction of hair growth. For example, the scalp often has a rounded surface due to the shape of the skull. By staggering the blades, the surgeon is more easily able to accommodate for the curved surface while trying to maintain the blades generally parallel to the direction of hair growth. Preferably, the surgeon will grasp the shaft with a pencil-like grip to facilitate the rapid production of the incisions.

DETAILED DESCRIPTION OF THE SPECIFIC EMBODIMENTS

Figure 3:
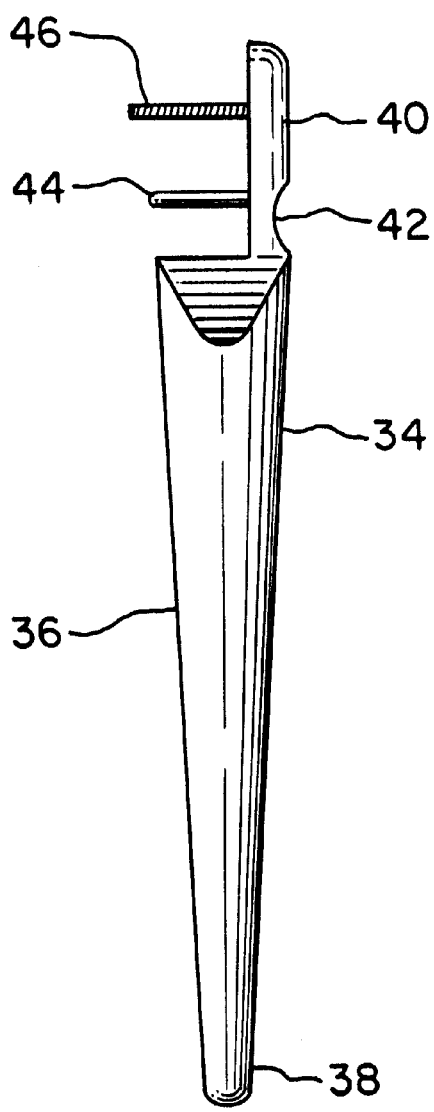
FIG. 3 illustrates a top view of an exemplary multiple blade holder according to the present invention.
Figure 4:
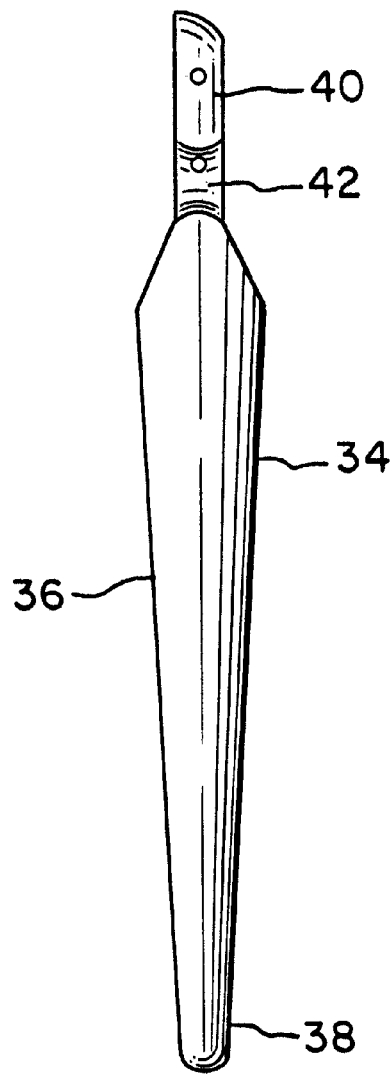
FIG. 4 illustrates a side view of the holder of FIG. 3.

The invention provides methods and apparatus for transplanting hair, and in particular for producing hair transplantation donor strips from which minigrafts or micrografts can be selected. The methods and apparatus of the invention allow for the production of hair transplantation donor strips without substantial destruction of the hairs in the strip as the strip is cut and removed from the scalp. An exemplary apparatus 34 for providing such a donor strip is shown in FIGS. 3 and 4. The apparatus 34 includes an elongate shaft 36 having a proximal end 38 and a distal end 40. The shaft 36 can be constructed of any rigid material, but will preferably be constructed of stainless steel. The exterior surface of the shaft 36 is preferably smooth so that the apparatus 34 can easily be cleaned. The proximal end 38 of the shaft 36 is tapered, with the proximal end 38 being smaller than the distal end 40. Tapering of the shaft 36 in this manner is advantageous in that the center of mass of the apparatus 34 is located near the distal end 40 of the apparatus 34. Centering of the mass near the distal end 40 is advantageous when the apparatus 34 is grasped and manipulated in an upright position as described in greater detail hereinafter. Use of stainless steel to construct the shaft 36 is desirable because the density of stainless steel accents the "feel" of the apparatus 34 in the surgeon's hand when the mass is centered near the distal end 40. A groove 42 is provided at the distal end 40 and is for receiving a finger of the surgeon when the apparatus 34 is grasped. The groove 42 allows for easier grasping and manipulation of the apparatus 34, and also serves as a reference point for the surgeon as described in greater detail hereinafter.

Figure 5:
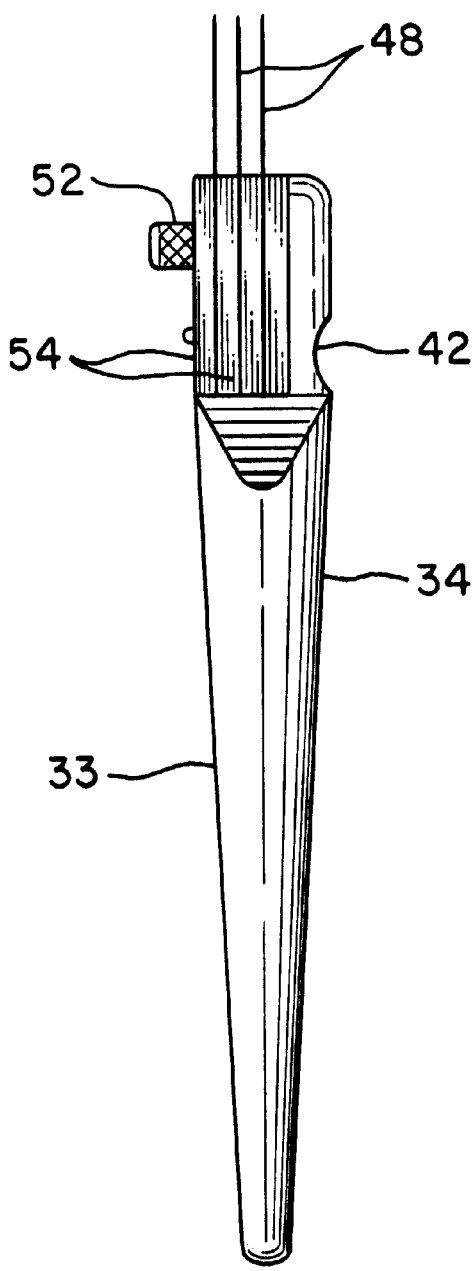
FIGS. 5 and 6 illustrate the holder of FIGS. 3 and 4, respectively, having a plurality of spaced-apart planar blades.
Figure 6:
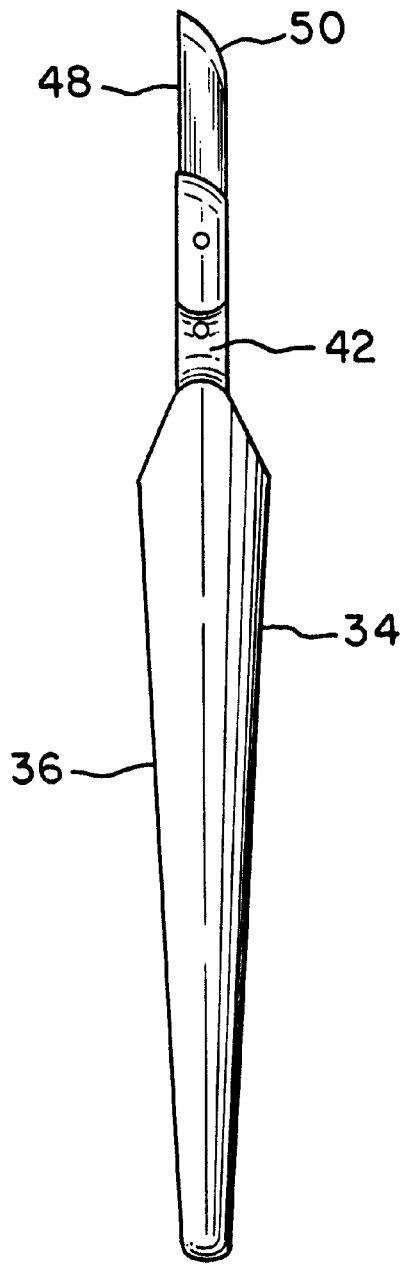

Two pins 44, 46 are provided at the distal end 40. The pin 46 is preferably threaded. As shown in FIGS. 5 and 6, a plurality of blades 48 are received over the pins 44, 46. Each of the blades has a sharpened edge 50 for forming incisions. The blades 48 are provided with apertures (not shown) so that they can be received over the pins 44, 46. The pins 44, 46 stabilize the blades 48 while a nut 52 is provided to secure the blades 48 to the distal end 40 of the shaft 36. A plurality of spacers 54 are provided for holding the blades 48 spaced-apart and parallel to each other. The blades 48 are available from a variety of suppliers including Persona Corporation.

The groove 42 is located on a side of the shaft 34 that is opposite the nut 52. As shown in the top view of FIG. 5, the groove 42 is on the right-hand side of the shaft 36 and the nut 52 is on the left-hand side. Such a configuration is designed for right-handed surgeons. A mirror image of the apparatus 34 can be provided for a left-handed surgeon.

The surgeon preferably grasps the apparatus 34 with the right hand and places the index finger on top of the blades 48 just left of the groove 42. The middle finger is received into the groove 42, while the thumb is positioned on the left side of the shaft 36. In this way, the apparatus 34 is held upright in a manner similar to holding a pencil or a pen. The groove 42 is preferably shaped in the form of an hourglass. Alternatively, the groove can be half round, i.e. semi-cylindrical, in geometry. As previously described, the groove 42 acts as a reference point so that the surgeon can hold the apparatus 34 the same each time. As the surgeon becomes more familiar with the apparatus 34, the groove 42 makes it easier for the surgeon to determine the location of the blades 48, and particularly the tips of the blades 48, relative to the patient's scalp. Providing the nut 52 on the left-hand side of the shaft 36 is advantageous in that the nut 52 does not interfere with the surgeons grasp when the apparatus 34 is held as just described.

A further advantage of tapering of the shaft 36 as previously described is that it allows the edges 50 of the blade 48 to face a table surface when the apparatus 34 is not in use. Optionally, the distal end 48 can have a flat bottom surface to provide stability when the apparatus 34 is set down and is not in use. This provides safety to the operating personnel by helping to ensure that the blades 48 will not accidently injure a person when the apparatus 34 is not in use.

Figure 7:
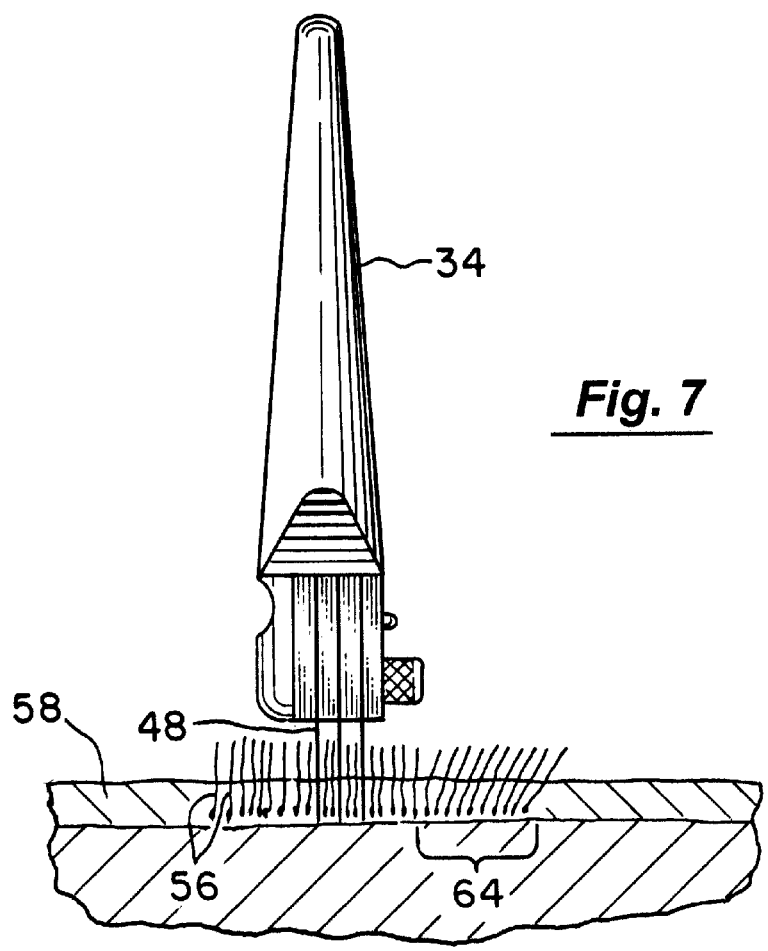
FIG. 7 illustrates an exemplary method for producing hair transplantation donor strips using the apparatus of FIGS. 5 and 6.

Referring to FIG. 7, an exemplary method for using the apparatus 34 to produce a hair transplantation donor strip will be described. When forming incisions, the blades 48 of the apparatus 34 are pressed into the scalp 58 so that the blades 48 are aligned parallel to the hairs 56 growing in the scalp 58. The blades 48 are then translated along and through the scalp while the orientation blades 48 relative to the hairs 56 are adjusted so that they remain generally parallel to the hairs 56 at all times. If the blades 48 are maintained generally parallel to the hairs 56, an elongate strip of skin 60 is produced as shown in cross-sectional view in FIG. 8. The hairs 56 in the strip 60 each contain a follicle 62 and can be used for subsequent transplantation.

Figure 9:
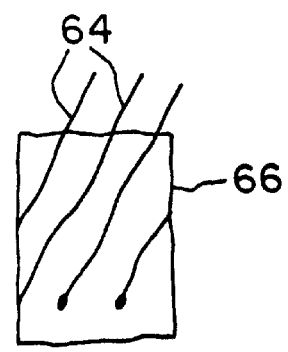
FIG. 9 illustrates a cross-sectional view of a hair transplantation donor strip produced when the incisions in the scalp were not parallel with the hairs in the graft.

Referring back to FIG. 7, a portion of hairs 64 extend from the scalp at an angle that is different than the rest of the hairs 56. If the apparatus 34 were translated through the scalp 58 at the location of the hairs 64 and at the same orientation shown in FIG. 7, a strip of skin 66 would be produced as shown in cross-sectional view in FIG. 9. Since the blades 48 would not be parallel with the hairs 64, some of the follicles 62 would be severed from the hairs 64 and would not be suitable for subsequent transplantation. This reduces the amount of viable hairs in the strip 66 that are available for transplantation.

Figure 1:
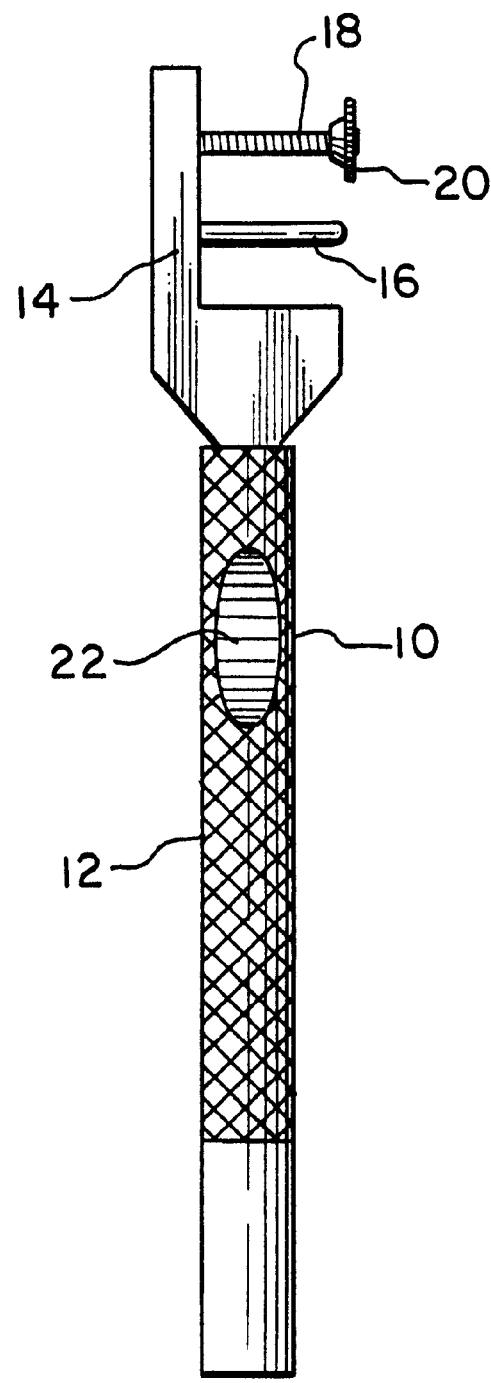
FIG. 1 illustrates a top view of a prior art multiple blade holder.
Figure 2:
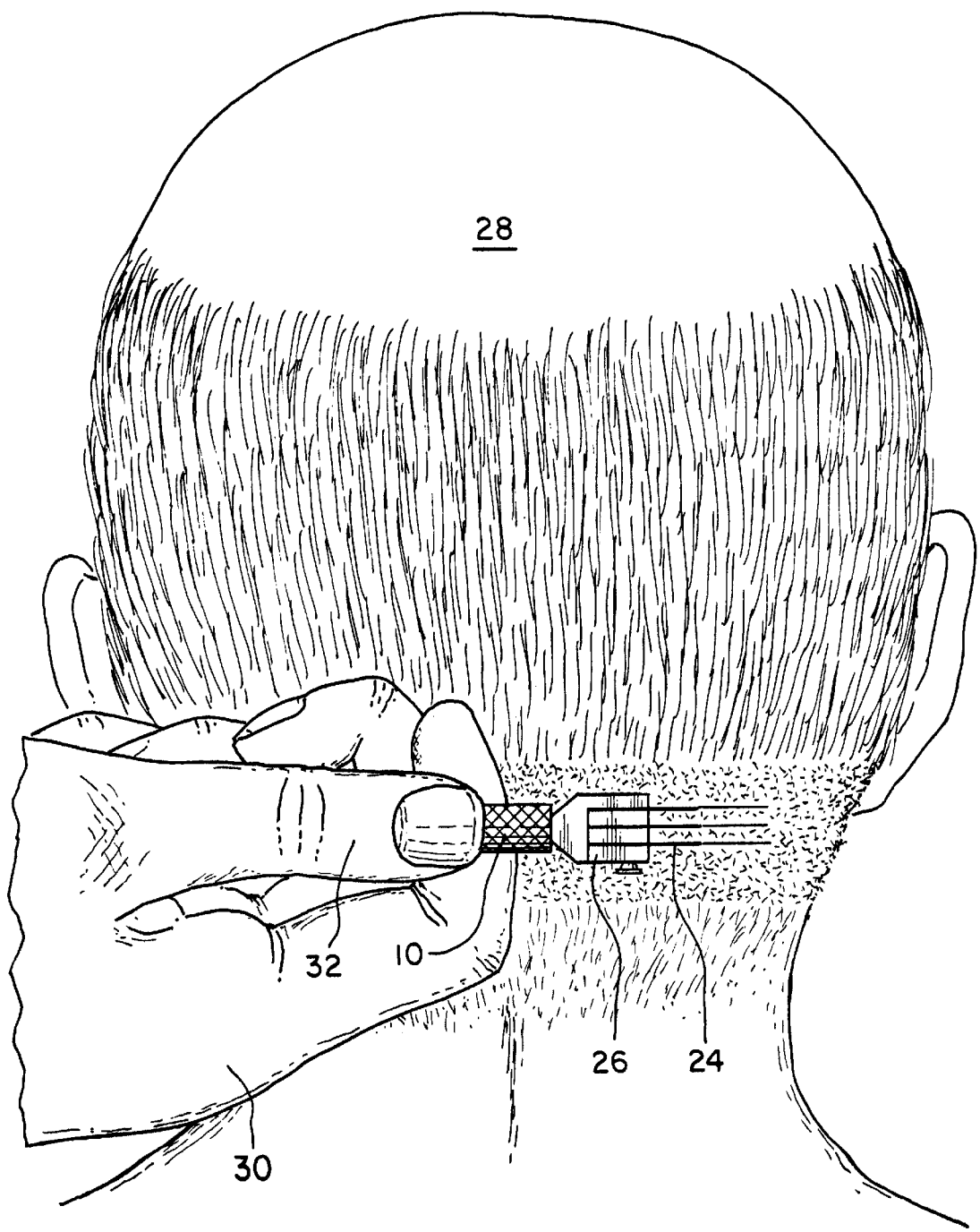
FIG. 2 illustrates a prior art method for producing hair transplantation donor strips using the apparatus of FIG. 1.
Figure 8:
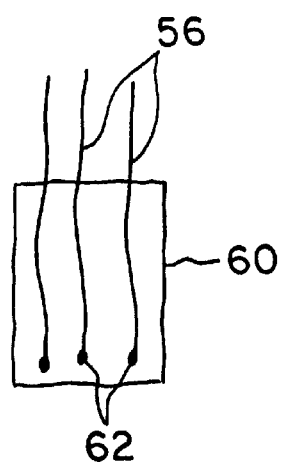
FIG. 8 illustrates a cross-sectional view of hair obtained from a hair transplantation donor strip produced in accordance with the principles of the present invention.
Figure 10:
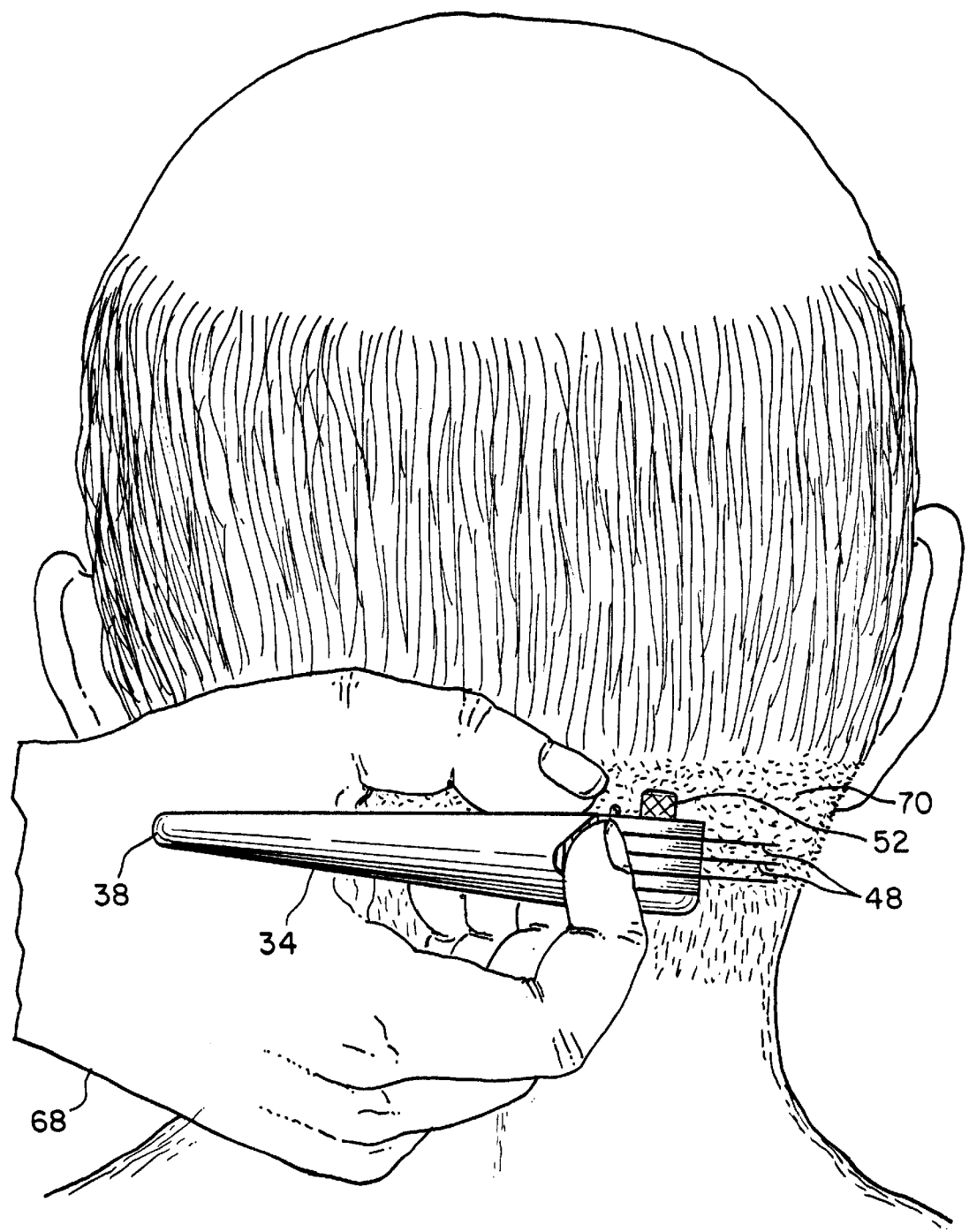
FIG. 10 illustrates an exemplary method for forming incisions in the scalp to produce an exemplary hair transplantation donor strip according to the principles of the present invention.

The invention provides a method for maintaining the blades 48 in an orientation that is generally aligned with the direction of hair growth in the scalp to produce donor strips as shown in FIG. 8. To produce such a strip, the apparatus 34 is grasped with the hand 68 as illustrated in FIG. 10. The apparatus 34 is held in a manner similar to holding a pen or pencil. In this way, the apparatus 34 is held generally upright, with the proximal end 38 being held above the hand 68. In contrast, the prior art method as illustrated in FIG. 2 orients the proximal end of the handle 12 beneath the hand 30. As previously described, the nut 52 is positioned away from the surgeon's fingers so that the apparatus 34 can more easily be grasped in such a manner. The groove 42 serves as a convenient resting place for one of the surgeon's fingers. The groove 42 also serves as a reference point for the surgeon.

After the apparatus 34 has been grasped as shown in FIG. 10, the blades 48 are positioned above the scalp 70 at a position where the incisions will be initiated. At this point, the surgeon rests the fourth finger, the side of the hand, and/or the wrist against the patient's scalp 70 so that orientation of the blades 48 can be accomplished by movement of the fingers and thumb and/or by rolling the hand and wrist. Before making any incisions, the surgeon evaluates the direction of hair growth at the position where the incisions are to be initially started. The surgeon then orients the position of the blades 48 so that they are aligned, i.e., generally parallel, with the hairs at that point. The blades 48 are then pressed into the scalp while maintaining the parallel orientation with the hairs. Once the blades 48 are within the scalp, the surgeon translates the fingers and the thumb toward the wrist to translate the blades 48 along and through the scalp 70. While translating the blades 48 through the scalp 70, the wrist or the side of the hand is maintained against the scalp 70 and is not axially translated. In this way, axial translation of the blades 48 is accomplished solely by movement of the fingers and thumb and not by axial translation of the arm. Translation of the fingers and thumb in this manner is advantageous because the orientation of the blades 48 relative to the scalp 70 can be precisely controlled. As the blades 48 are being translated through the scalp 70, the surgeon continually evaluates the orientation of the hairs growing in the scalp. As the direction of the hairs changes, the surgeon readjusts the orientation of the blades 48 relative to the hairs so that the blades 48 remain parallel to the hairs between the blades at all times during translation. This can be accomplished by movement of the fingers and thumb and/or by rolling the hand while it rests on the scalp 70.

Since the hand 68 remains fixed relative to the scalp 70, the length of the incisions formed by the blades 48 is limited. Usually, an incision having a length of about 2 cm to 3 cm can be made with one stroke of the fingers and thumb while the wrist remains fixed. To increase the length of the incisions, the surgeon ceases translation of the blades 48 and moves the hand 68 further back on the patient's scalp 70 and axially way from the incisions. While maintaining the hand 68 in the new position, the fingers and thumb are again translated to continue translation of the blades 48 along and through the scalp 70. While continuing to pass the blades 48 through the scalp 70, the surgeon continually readjusts the orientation of the blades 48 relative to the direction of hair growth in the scalp 70 so that the hairs between the blades 48 are not destroyed. This process is repeated as many times as necessary until the incisions reach the desired length. For most procedures, the length of the incisions will be in the range from about 5 cm to 20 cm. The apparatus 34 is then removed from the scalp 70 and the skin between the incisions is removed from the scalp 70 in elongate strips. The skin is removed from the scalp by grasping and lift the skin with forceps while separating the skin from the scalp 70 with a scalpel blade or scissors. The hair transplantation donor strips can then be cut into smaller skin grafts, usually having about 1 to 6 hairs, which are then transplanted into another area of the scalp 70.

By providing a series of precisely controlled movements without axial translation of the hand and arm, the present invention produces hair transplantation donor strips having little or no hairs destroyed. The short, concise strokes are advantageous over the prior art method where a single rapid stroke is made along the length of the scalp and which does not take into consideration the direction of hair growth in the scalp. The invention therefore prevents the destruction of hairs that could otherwise be used in the transplantation procedure.

Figure 11:
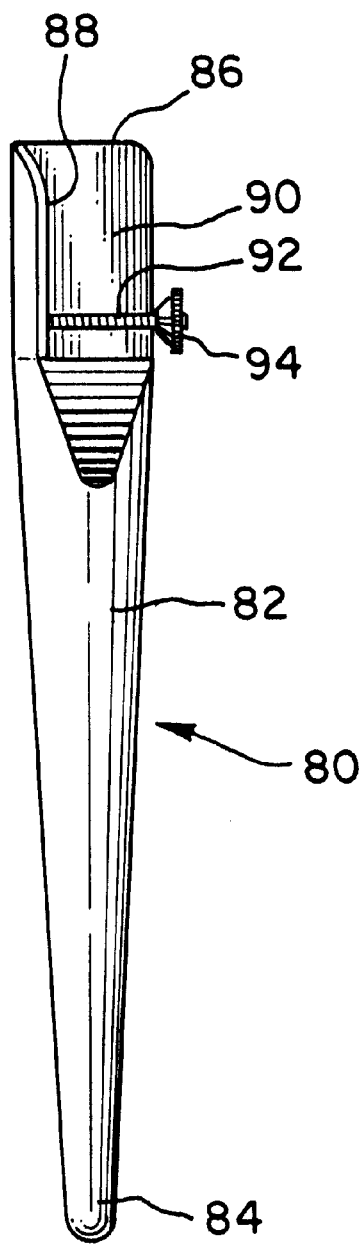
FIG. 11 is a perspective side view of an alternative multiple blade holder according to the invention.

Referring now to FIG. 11, another exemplary embodiment of a multiple blade holder 80 will be described. Holder 80 comprises an elongate shaft 82 having a proximal end 84 and a distal end 86. At distal end 86 are a pair of orthogonal surfaces 88 and 90. Hence, multiple blade holder 80 is similar to apparatus 34 except for the addition of surface 90. Holder 80 further includes a single threaded pin 92 and a nut 94. Pin 92 is provided so that a plurality of blades having elongate slots may be inserted over pin, while nut 94 may be tightened to cinch the blades to surface 88. In this manner, the blades will be essentially parallel to surface 88.

Figure 12:
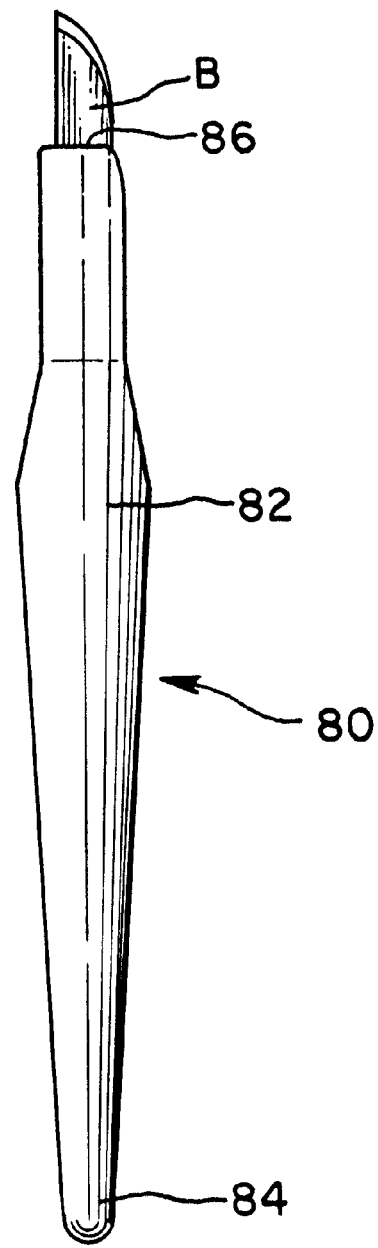
FIG. 12 is a side view of the holder of FIG. 11 having a plurality of blades attached thereto.

As best shown in FIG. 12, when a plurality of blades B are attached to shaft 82, a top end of the blades will be adjacent surface 90. This configuration is advantageous in that only a single pin may be employed to securely hold blades B to shaft 82, with surface 90 (in combination with pin 92) preventing rotation of blades B when making an incision.

Figure 13:
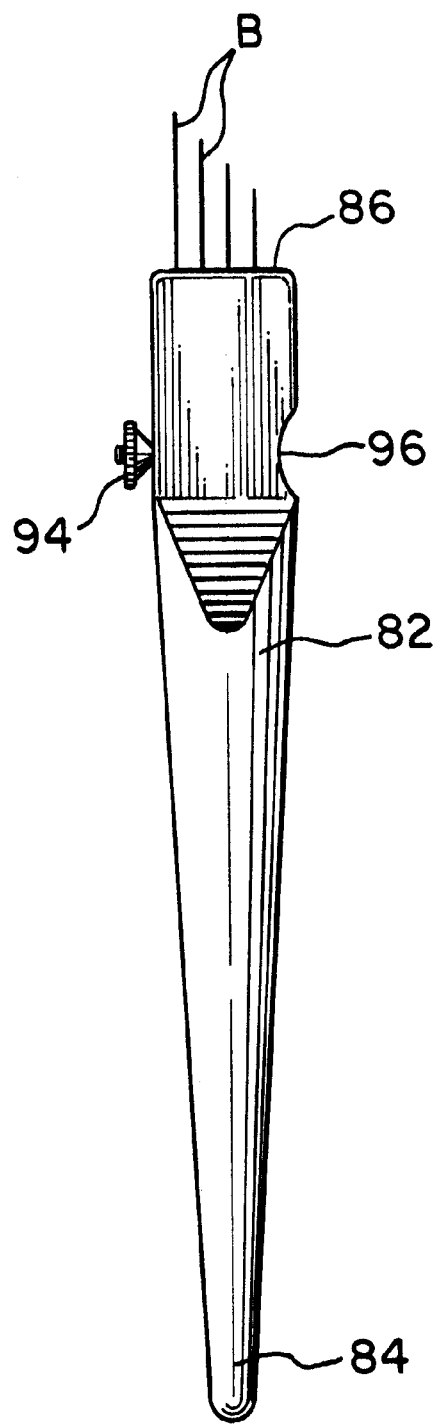
FIG. 13 is a side plan view of the holder of FIG. 11 with a plurality of staggered blades according to the invention.

Such a configuration is further advantageous in that blades B may be staggered, or otherwise adjusted, by simply sliding each blade over pin 92 while nut 94 is loosened. One, such staggered configuration is illustrated in FIG. 13. Once the desired configuration for the blades B is obtained, nut 94 is rotated to secure the blades to shaft 82.

Staggering of the blades as illustrated in FIG. 13 is advantageous in that a surgeon may accommodate for unlevel areas of skin without having to extensively manipulate shaft 82. To make a plurality of parallel incisions with such an arrangement, the surgeon simply grasps shaft 82 with a pencil-like grip as previously described and translates the blades B through the skin with shaft 82 being in substantially a vertical orientation, with the staggering of blades B accommodating for any angling of the skin. In this way, elongate parallel incisions may be rapidly made, with the incisions being generally parallel to the direction of hair growth so that the future hair grafts will not be destroyed.

Advantageously, shaft 82 is tapered from distal end 86 to proximal end 84 similar to the embodiments previously described to place the center of mass near where the surgeon grasps the instrument. In this way, a surgeon will be better able to manipulate and become accustomed to the "feel" of the instrument. As with other embodiments, shaft 82 may optionally be provided with a finger groove 96 to accommodate the surgeon's finger when grasping the device with a pencil-like grip.

Although shown with a threaded pin and a nut, it will be appreciated that other securing mechanisms may be employed to hold blades B to shaft 82. For example, various clamping mechanisms and the like may be employed. Further, as with other embodiments, spacers will preferably be provided between blades B to keep their spaced apart relationship. Also as with other embodiments, shaft 82 will preferably be constructed from stainless steel. Although shown with only a single pin 92, it will be appreciated that in some cases more than one pin may also be used. However, use of a single pin is preferred since it allows for easier adjustment of the blades as previously described.

Although the foregoing invention has been described in some detail by way of illustration and example, for purposes of clarity of understanding, it will be obvious that certain changes and modifications may be practiced within the scope of the appended claims.

What is claimed is:

1. A surgical apparatus, comprising:

an elongate shaft having a proximal end and a distal end;

at least two surfaces at the distal end;

a plurality of parallel spaced-apart planar blades at the distal end of the shaft, wherein each blade has a proximal end, a distal end, a top and a bottom opposite the top, wherein the bottom of each blade has a sharpened edge, and wherein the distal ends of the blades are staggered relative to each other, with one of the surfaces being above the top of each of the blades to prevent the blades from rotating;

a securing mechanism operably attached to one of the surfaces, wherein the securing mechanism is adapted to secure the blades to the distal end of the shaft in a parallel and spaced-apart manner; and at least one spacer which is adapted to maintain the blades spaced-apart.

2. An apparatus as in claim 1, wherein the surface having the securing mechanism attached thereto is adapted to be parallel with the blades.

3. An apparatus as in claim 2, wherein the two surfaces are orthogonal to each other.

4. A surgical apparatus for forming parallel incisions in the skin, comprising:

an elongate shaft having a proximal end and a distal end;

at least two intersecting surfaces at the distal end;

a plurality of parallel spaced-apart planar blades at the distal end of the shaft, wherein each blade has a proximal end, a distal end, a top and a bottom opposite the top, wherein the bottom of each blade has a sharpened edge, and wherein the distal ends of the blades are staggered relative to each other, with one of the surfaces being above the top of each of the blades to prevent the blades from rotating.

5. An apparatus as in claim 4, further comprising a securing mechanism which holds the blades to at least one of the surfaces.

6. An apparatus as in claim 5, wherein each of the blades includes a slot therein, and wherein the securing mechanism comprises a single threaded pin extending from one of the surfaces over which the blades are received and a nut.

7. An apparatus as in claim 6, wherein the surface having the securing mechanism attached thereto is parallel with the blades.

8. An apparatus as in claim 7, wherein the surfaces are orthogonal to each other.

9. An apparatus as in claim 4, further comprising at least one spacer to maintain the blades spaced-apart.

10. An apparatus as in claim 4, wherein the shaft tapers from the distal end to the proximal end.

11. A method for forming parallel incisions in the skin, comprising:

providing a surgical device comprising an elongate shaft having a proximal end and a distal end, wherein the distal end includes at least two surfaces;

removably attaching a plurality of blades to the distal end, with the blades being spaced-apart and parallel to each other, and with one of the surfaces being disposed over a top of each of the blades;

translating the blades through the skin to form a plurality of parallel incisions in the skin; and wherein each of the blades includes a slot therein, and wherein the surgical device further includes a securing mechanism comprising a threaded pin extending from one of the surfaces, and further comprising inserting the pin through the slots and securing the blades to one of the surfaces with a nut.

12. A method as in claim 11, wherein the surface having the securing mechanism attached thereto is parallel with the blades.

13. A method as in claim 11, further comprising adjusting the blades along the pin so that the blades are staggered relative to each other.

14. A method as in claim 7, wherein the surfaces are orthogonal to each other.

15. A method as in claim 11, wherein the shaft is tapered, and further comprising grasping the shaft with a pencil like grip.

16. A method as in claim 11, further comprising translating the blades through the skin in an orientation substantially parallel with the direction of hair growth.

17. A surgical apparatus, comprising:

an elongate shaft having a proximal end and a distal end;

at least two surfaces at the distal end;

a securing mechanism operably attached to one of the surfaces, wherein the securing mechanism is adapted to secure a plurality of adjustable blades to the distal end in a parallel and spaced-apart manner, with one of the surfaces being adapted to prevent rotation of the blades when secured to the distal end; and wherein the surface which is adapted to prevent rotation of the blades is adapted to be positioned so as to be over a top surface of each of the blades;

wherein each of the blades includes a slot therein, and wherein the securing mechanism comprises a threaded pin extending from one of the surfaces over which the blades are received and a nut, whereby the blades may be adjusted by moving them over the pin to place the blades in a staggered relationship.

18. A method for forming parallel incisions in the skin, comprising:

providing a surgical device comprising an elongate shaft having a proximal end and a distal end, wherein the distal end includes at least two surfaces;

removably attaching a plurality of blades to the distal end, with the blades being spaced-apart and parallel to each other, and with one of the surfaces being disposed over a top of each of the blades;

translating the blades through the skin in an orientation substantially parallel with the direction of hair growth to form a plurality of parallel incisions in the skin.

* * * * *